(12) United States Patent
Yamaguchi et al.

(10) Patent No.: US 11,576,997 B2
(45) Date of Patent: Feb. 14, 2023

(54) IODINE-LOADED BONE REPAIR MATERIAL AND METHOD FOR PRODUCING THE SAME

(71) Applicant: CHUBU UNIVERSITY EDUCATIONAL FOUNDATION, Kasugai (JP)

(72) Inventors: Seiji Yamaguchi, Kasugai (JP); Morihiro Ito, Kasugai (JP); Takashi Nakamura, Kyoto (JP)

(73) Assignee: CHUBU UNIVERSITY EDUCATIONAL FOUNDATION, Aichi (JP)

( * ) Notice: Subject to any disclaimer, the term of this patent is extended or adjusted under 35 U.S.C. 154(b) by 0 days.

(21) Appl. No.: 16/977,555

(22) PCT Filed: Mar. 1, 2019

(86) PCT No.: PCT/JP2019/008070
§ 371 (c)(1),
(2) Date: Sep. 2, 2020

(87) PCT Pub. No.: WO2019/172116
PCT Pub. Date: Sep. 12, 2019

(65) Prior Publication Data
US 2021/0001004 A1      Jan. 7, 2021

(30) Foreign Application Priority Data

Mar. 5, 2018   (JP) .............................. JP2018-038983

(51) Int. Cl.
*A61L 27/06*   (2006.01)
*A61L 27/02*   (2006.01)

(52) U.S. Cl.
CPC ............. *A61L 27/06* (2013.01); *A61L 27/025* (2013.01); *A61L 2420/02* (2013.01)

(58) Field of Classification Search
CPC ...... A61M 25/00; A61L 27/06; A61L 27/025; A61F 2/28
See application file for complete search history.

(56) References Cited

U.S. PATENT DOCUMENTS

| | | |
|---|---|---|
| 8,470,387 B2 | 6/2013 | Kokubo et al. |
| 9,034,051 B2 | 5/2015 | Kokubo et al. |

(Continued)

FOREIGN PATENT DOCUMENTS

| | | |
|---|---|---|
| JP | 2932437 B1 | 8/1999 |
| JP | 2008-73098 A | 4/2008 |

(Continued)

OTHER PUBLICATIONS

Su et al., Synergistic effect of nanotopography and bioactive ions on peri-implant bone response, Jan. 2017, International Journal of Nanomedicine, vol. 12, pp. 925-934 (Year: 2017).*

(Continued)

*Primary Examiner* — Dah-Wei D. Yuan
*Assistant Examiner* — Andrew J Bowman
(74) *Attorney, Agent, or Firm* — WHDA, LLP

(57) ABSTRACT

A highly safe and inexpensive bone repair material that stably exhibits high antibacterial activity for a long time in a living body by supporting a large amount of an iodine ion and is excellent in apatite forming ability and preservability. The material includes a substrate made of titanium or titanium alloy and a titanate film on a surface of the substrate, the film composed of a large number of crystalline masses having a crystal structure and containing a calcium ion and an iodine ion, wherein the mass contains layers having a Ti—O skeleton and the calcium and the iodine ions adsorbed between the layers.

7 Claims, 7 Drawing Sheets

(56) References Cited

U.S. PATENT DOCUMENTS

2003/0215484 A1* 11/2003 Axen .................... C04B 41/009
                                                              424/423
2008/0020127 A1*  1/2008 Whiteford ............... A61L 29/16
                                                              427/2.1

FOREIGN PATENT DOCUMENTS

| JP | 5499347 B2 | 5/2014 |
|---|---|---|
| WO | 2008/081861 A1 | 7/2008 |
| WO | 2010/087427 A1 | 8/2010 |

OTHER PUBLICATIONS

E1, Calcium titanate, 2022, Wikipedia, pp. 1-2 (Year: 2022).*

De Viteri et al., Structure tribocorrosion and biocide characterization of Ca, P and I containing TiO2 coatings developed by plasma electrolytic oxidation, 2016, Applied Surface Science, vol. 367, pp. 1-10 (Year: 2016).*

Hashimoto et al., "Antimicrobial Characteristics of Anodic Oxidation Coating of Aluminum Impregnated with Iodine Compound", Inorganic Materials, 1999, vol. 6, pp. 457-462, cited in Specification, w/English abstract (6 pages).

Spriano et al., "A critical review of multifunctional titanium surfaces: New frontiers for improving osseointegration and host response, avoiding bacteria contamination", Acta Biomaterialia, 2018, vol. 79, pp. 1-22, cited in Specification (22 pages).

De Viteri et al., "Structure, tribocorrosion and biocide characterization of Ca, P and I containing TiO2 coatings developed by plasma electrolytic oxidation", Applied Surface Science, 2016, vol. 367, pp. 1-10, cited in ISR (10 pages).

Taga et al., "Comparison with the osteoconductivity and bone-bonding ability of the iodine supported titanium, titanium with porous oxide layer and the titanium alloy in the rabbit model", Journal of Orthopaedic Science, 2018, vol. 23, pp. 585-591, cited in ISR (7 pages).

Tsuchiya et al., "Innovative antimicrobial coating of titanium implants with iodine", J Orthop Sci, 2012, vol. 17, pp. 595-604, cited in ISR (10 pages).

International Search Report dated Apr. 9, 2019, issued in counterpart International Application No. PCT/JP2019/008070 (1 page).

* cited by examiner

IODINE-LOADED BONE REPAIR MATERIAL AND METHOD FOR PRODUCING THE SAME

TECHNICAL FIELD

The present invention relates to an iodine-loaded bone repair material and a method for producing the same. The bone repair material can be suitably used for repair of a bone where a large load is applied, such as a femur, a hip joint, a spine, or a tooth root.

BACKGROUND ART

Titanium or titanium alloy has high fracture toughness and is biocompatible, and hence is widely used as a bone repair material for a portion where a large load is applied such as an artificial joint or an artificial vertebral body. In order to impart osteoconnectivity to titanium or titanium alloy, various methods for forming an apatite layer on a surface of a substrate made of titanium or titanium alloy have been examined. Among these methods, a bone repair material containing titanium or alloy thereof having, on its surface, a titanate layer or a titanium oxide layer with apatite forming ability forms apatite in a living body, and hence is said to be excellent in that the thus formed apatite is not cracked by dryness or thermal expansion difference from a substrate (Patent Document 1&2).

On the other hand, when an infectious disease is caused after embedding a bone repair material in the living body, it is difficult to treat the disease with an antibiotic. Therefore, various techniques for imparting antibacterial activity to a bone repair material have been proposed. For example, since silver has been known as an element exhibiting remarkably high antibacterial activity from a long time ago, a technique for replacing an alkali component contained in a titanate layer with a silver ion (Patent Document 3), and a technique for forming a coating film of a mixture of calcium phosphate and silver oxide on a surface of a titanium substrate (Patent Document 4) have been published. When silver is introduced into a bone repair material in the form of a metal particle, it is apprehended that the silver particle falls off from the surface of the material to accumulate in an unexpected organ to cause cytotoxicity, and hence, silver is introduced in the form of an ion or an oxide. A pharmaceutical containing a silver fine particle was once approved by US Department of Health and Human Services (FDA), but is currently prohibited because a high intake of such a pharmaceutical causes argyria. Besides, since it has been reported that iodine exhibits antibacterial activity as high as that of silver against MRSA and *E. coli* (Non-Patent Document 1), a technique for causing iodine to be contained in a micropore formed in a metal surface by electrodeposition has also been published (Patent Document 5).

RELATED ART DOCUMENTS

Patent Documents

Patent Document 1: Japanese Patent No. 5499347
Patent Document 2: WO2010/087427
Patent Document 3: WO2008/081861
Patent Document 4: Japanese Patent Laid-Open No. 2008-73098
Patent Document 5: Japanese Patent No. 2932437

Non-Patent Documents

Non-Patent Document 1: K. Hashimoto et al., Inorganic Materials, 6 (1999) 457-462
Non-Patent Document 2: S. Spriano, et al., Acta Biomater. 10 (2018) 557

SUMMARY OF THE INVENTION

Problems to be Solved by the Invention

Even when silver is introduced in the form of an ion as described in Patent Document 3, however, a titanium metal or titanium alloy into which silver has been introduced exhibits high antibacterial activity and does not exhibit cytotoxicity merely in a narrow range of a silver ion concentration of 0.27 to 0.6% (Non-Patent Document 2), and hence this method is not suitable for mass production. A material obtained by the method described in Patent Document 4 elutes an antibacterial agent while dissolving calcium phosphate contained in a coating member, and hence cannot be firmly bonded to a bone tissue. Therefore, this material is inferior in initial fixability, and hence a bone repair treatment takes a long time.

For obtaining a material by the method described in Patent Document 5, iodine needs to be moved by electrophoresis into the micropore of the substrate by electrodeposition, which requires an expensive apparatus. Besides, the material obtained by this method supports, on its surface, merely a small amount of iodine of about 0.1% by mass. Therefore, it is apprehended that the material may be deactivated through a long-term storage, and even when the material is embedded in the body before deactivation, the antibacterial effect cannot be expected to last for a long period of time. Besides, when the substrate is porous or in a complicated shape, charge is not distributed within a recess due to electrostatic shielding, and hence iodine is difficult to be uniformly supported by this method.

Accordingly, an object of the present invention is to inexpensively provide a highly safe bone repair material that stably exhibits high antibacterial activity for a long period of time in the living body by supporting a large amount of an iodine ion, and is excellent in apatite forming ability and preservability.

Means of Solving the Problems

In order to solve the problem, a bone repair material of the present invention includes: a substrate made of titanium or titanium alloy; and a titanate film on a surface of the substrate, the titanate film composed of a large number of crystalline masses having a crystal structure, and containing a calcium ion and an iodine ion. The crystalline mass may be in the form of a column, a flake, a scale, a granule, a needle or the like. The iodine ion may be an anion, namely, an iodide ion, or may be a cation.

When this bone repair material is used, since the titanate film contains both the calcium ion and the iodine ion, the iodine ion contained in the titanate film exhibit antibacterial activity in the living body, and at the same time, the calcium ion exhibits apatite forming ability in the living body, so that the material can be bonded to a bone.

The crystalline mass contains: a plurality of layers usually having a Ti—O skeleton; and the calcium ion and the iodine ion adsorbed between these layers. Assuming that the crystalline mass is in the form of a column, for example, in a preferable aspect of the bone repair material of the present invention, each of a large number of columnar crystalline masses extending in a direction crossing the principal plane of a substrate as illustrated in FIG. 1(a) consists of a plurality of layers overlapping one another as illustrated in FIG. 1(b), and the calcium ion and the iodine ion are both contained between these layers. Therefore, these ions are controlled-released through diffusion within the crystal, and thus, the antibacterial activity and the osteoconnectivity can be exhibited for a long period of time.

A suitable method for producing the bone repair material of the present invention includes: immersing a substrate made of titanium or titanium alloy in a first alkaline aqueous solution that does not contain a calcium ion or an iodine ion but contains one or more types of cations selected from a sodium ion and a potassium ion; immersing the substrate in a second aqueous solution containing a calcium ion; heating the substrate in a dry atmosphere; and immersing the substrate in a third aqueous solution containing an iodine ion.

When the substrate is immersed in the first aqueous solution, titanium contained in the substrate reacts with the aqueous solution to form a film of sodium hydrogen titanate or potassium hydrogen titanate on a surface of the substrate. Subsequently, when the resultant substrate is immersed in the second aqueous solution, a sodium or potassium ion contained in the film of sodium hydrogen titanate or potassium hydrogen titanate is exchanged for the calcium ion contained in the aqueous solution.

When the resultant substrate is heated in the air, the film is dehydrated to form a mechanically and chemically stable anhydrous titanate film, and thus, scratch resistance is remarkably improved.

Thereafter, when the substrate is immersed in the third aqueous solution, a part of the calcium ion contained in the film is exchanged for an iodine ion and a hydronium ion, and a void is formed in a position from which the calcium ion has been removed, so that a remaining calcium ion easily elutes into the living body. As a result, the surface of the substrate is activated sufficiently for exhibiting apatite forming ability, and in addition, the activity is retained through a long-term storage in high humidity. An amount of the iodine ion contained in this film is usually as large as 0.5% by mass or more, and hence the resultant material can withstand long-term storage, and in addition, exhibits the antibacterial effect in the living body for a long period of time.

When the iodine ion contained in the third aqueous solution is positively charged, the exchange for the calcium ion easily proceeds. A positively charged iodine ion is produced by dissolving, in water, a compound of iodine monochloride, iodine trichloride, hypoiodous acid, iodine monofluoride, iodine trifluoride, iodine pentafluoride, iodine heptafluoride, iodine monobromide, iodine tribromide, or the like.

Effects of the Invention

As described so far, the bone repair material obtained by the present invention can rapidly bond to a bone in a living body to repair a bone defect portion when embedded in the living body, can prevent or treat an infectious disease, and is excellent in preservability, and therefore can be stocked for operations.

MODE FOR CARRYING OUT THE INVENTION

Figure 1:
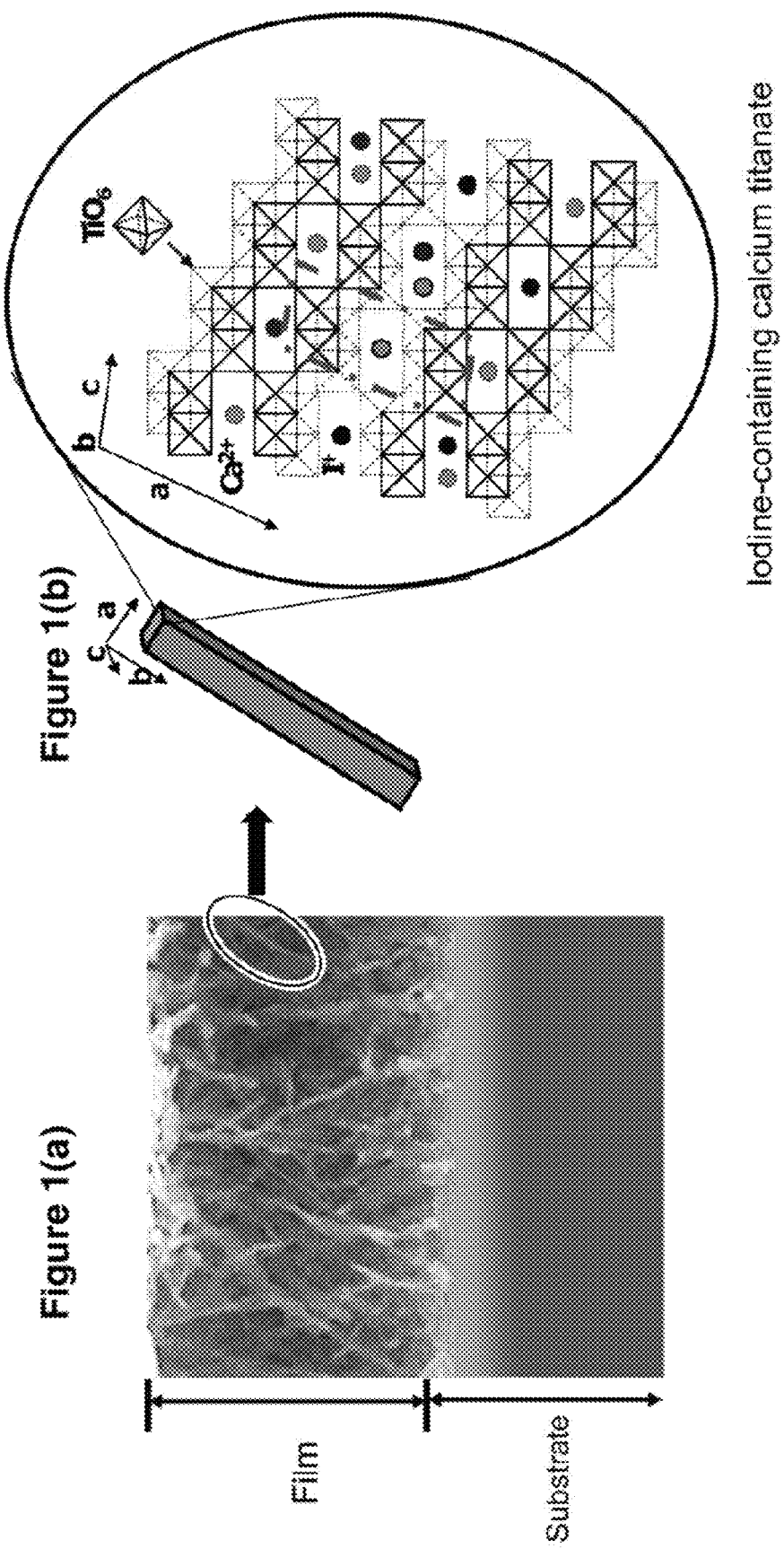
FIG. 1(a) is an electron micrograph of a cross-section of a bone repair material of the present invention.
FIG. 1(b) is a schematic diagram of a structure of one columnar crystalline mass present in the cross-section.

The above-described film usually has a thickness of 0.1 to 10 μm. When the thickness falls within this range, the film usually has a calcium ion concentration of 0.1 to 10% by mass and an iodine ion concentration of 0.1 to 15% by mass, and simultaneously exhibits apatite forming ability and antibacterial activity. In order to induce adequate apatite forming ability, the calcium ion concentration is preferably 1 to 7% by mass, and in order to obtain antibacterial effect in a living body for a long period of time, the iodine ion concentration is preferably 1 to 15% by mass.

The concentration of calcium ion in a second aqueous solution is usually in a range of 0.01 to 5000 mM, and is preferably 0.01 to 100 mM. When the concentration falls within the preferable range, it is easy to introduce, into the film, a calcium ion and a bone-forming ion at the preferable concentrations.

A temperature of the second aqueous solution and an immersion time employed in immersing the substrate are usually 20° C. or more and 0.5 hours or more, respectively, and preferably 40° C. or more and 24 hours or more, respectively. When the preferable temperature and immersion time are employed, it is easy to introduce, into the film, a calcium ion at the preferable concentration.

A temperature and a retention time for heating the substrate in the air are usually 400° C. or more and 0.5 hours or more, respectively, and preferably 600° C. or more and 1 hour or more, respectively. When the preferable heating temperature and retention time are employed, scratch resistance of the film is easily increased to 10 mN or more.

An iodine ion concentration of an iodine compound used for preparing a third aqueous solution is usually 1 to 1000 mM, and preferably 10 to 100 mM. When the preferable concentration is employed, it is easy to introduce, into the film, an iodine ion at the preferable concentration without largely changing the thickness of the film.

A temperature of the third aqueous solution and an immersion time employed in immersing the substrate are usually 40° C. or more and 3 hours or more, respectively, and preferably 60° C. or more and 24 hours or more, respectively. When the preferable immersion temperature and immersion time are employed, it is easy to activate the film, such that apatite can be formed on 50% or more of the surface in a simulated body fluid within 3 days.

When the concentration of the iodine ion in the third aqueous solution is changed, the iodine concentration of the film can be changed.

EXAMPLES

Example 1

A pure titanium plate (substrate) having a size of 10 mm×10 mm×1 mm was polished with a #400 diamond pad, was ultrasonically washed with acetone, 2-propanol, and ultrapure water each for 30 minutes, was then immersed in 5 ml of a 5 M sodium hydroxide aqueous solution at 60° C. for 24 hours (hereinafter, referred to as an "alkali treatment"), and was washed with ultrapure water for 30 seconds. The resultant titanium plate was immersed in 10 ml of a 100 mM calcium chloride aqueous solution at 40° C. for 24 hours (hereinafter, referred to as a "calcium treatment"), and was washed with ultrapure water for 30 seconds. Subsequently, the resultant titanium plate was heated in an electric furnace with the temperature increased from normal temperature to 600° C. at a rate of 5° C./min, was retained in the air at 600° C. for 1 hour, and was cooled in the furnace (hereinafter, referred to as a "heat treatment"). Thereafter, the titanium plate was immersed in 10 ml of a 10 mM iodine trichloride aqueous solution at 80° C. for 24 hours (hereinafter, referred to as an "iodine treatment"), and was washed with ultrapure water for 30 seconds. Thus, a sample was produced.

Example 2

A sample was produced under the same conditions as in Example 1 except that a 100 mM iodine trichloride aqueous solution was used instead of the 10 mM iodine trichloride aqueous solution in the iodine treatment of Example 1.

Example 3

A sample was produced under the same conditions as in Example 2 except that the immersion temperature was changed to 60° C. in the iodine treatment of Example 2.

Example 4

A sample was produced under the same conditions as in Example 2 except that the immersion temperature was changed to 40° C. in the iodine treatment of Example 2.

Example 5

A sample was produced under the same conditions as in Example 1 except that a 1871 mM iodine monochloride aqueous solution was used instead of the 10 mM iodine trichloride aqueous solution and the immersion temperature was changed to 60° C. in the iodine treatment of Example 1.

Example 6

A sample was produced under the same conditions as in Example 1 except that a Ti-6Al-4V alloy plate was used instead of the pure titanium plate of Example 1, and that the immersion temperature was changed to 95° C. in the alkali treatment.

Example 7

A sample was produced under the same conditions in Example 1 except that a Ti-15Zr-4Nb-4Ta alloy plate was used instead of the pure titanium plate of Example 1.

Comparative Example 1

A sample was produced under the same conditions as in Example 1 except that a 1000 ppm polyvinylpyrrolidone-iodine aqueous solution was used instead of the 10 mM iodine trichloride aqueous solution and the immersion temperature was changed to 60° C. in the iodine treatment of Example 1.

Comparative Example 2

A sample was produced under the same conditions as in Example 1 except that a 100 mM sodium iodide aqueous solution was used instead of the 10 mM iodine trichloride aqueous solution and the immersion temperature was changed to 60° C. in the iodine treatment of Example 1.

Comparative Example 3

A sample was produced by immersing a plate in 10 ml of a 10 mM iodine trichloride aqueous solution at 40° C. for 24 hours after the alkali treatment of Example 1 without performing the calcium treatment and the heat treatment.

Comparative Example 4

A sample was produced in the same manner as in Comparative Example 3 except that the heat treatment was performed.

Comparative Example 5

A sample was produced by immersing a plate in 10 ml of a 1000 ppm polyvinylpyrrolidone-iodine aqueous solution at 40° C. for 24 hours after the alkali treatment of Example 1 without performing the calcium treatment and the heat treatment.

Comparative Example 6

After performing the alkali treatment of Example 1, the resultant plate was immersed in 10 ml of a 50 mM hydrochloric acid at 40° C. for 24 hours (hereinafter, referred to as an "acid treatment"), the heat treatment of Example 1 was performed, the resultant was then immersed in a 1000 ppm polyvinylpyrrolidone-iodine aqueous solution to make a resultant plate an anode, and a voltage of 150 V was applied to the resultant plate for 3 minutes (hereinafter, referred to as an "electrodeposition treatment"). Thus, a sample was produced. The sample of this comparative example corresponds to a material obtained by performing alkali, acid, and heat treatments described in Patent Document 2, and then subjecting the resultant to an electrodeposition treatment described in Patent Document 5.

The production conditions for the samples of the examples and comparative examples described above are all shown in Table 1 below.

TABLE 1

| Sample[1] | Substrate | Alkali treatment | Calcium/Iodine/Acid treatment | Heat treatment | Iodine,/Electrodeposition treatment |
|---|---|---|---|---|---|
| E1 | Ti | [2] | 100 mM CaCl$_2$, 10 ml, 40° C., 24 hr | 600° C.(5° C./min), 1 hr | 10 mM ICl$_3$, 10 ml, 80° C., 24 hr |
| E2 | Ti | | 100 mM CaCl$_2$, 10 ml, 40° C., 24 hr | 600° C.(5° C./min), 1 hr | 100 mM ICl$_3$, 10 ml, 80° C., 24 hr |
| E3 | Ti | [2] | 100 mM CaCl$_2$, 10 ml, 40° C., 24 hr | 600° C.(5° C./min), 1 hr | 100 mM ICl$_3$, 10 ml, 60° C., 24 hr |
| E4 | Ti | | 100 mM CaCl$_2$, 10 ml, 40° C., 24 hr | 600° C.(5° C./min), 1 hr | 100 mM ICl$_3$, 10 ml, 40° C., 24 hr |
| E5 | Ti | | 100 mM CaCl$_2$, 10 ml, 40° C., 24 hr | 600° C.(5° C./min), 1 hr | 1871 mM ICl$_3$, 10 ml, 60° C., 24 hr |
| E6 | Ti—6Al—4V | [2] | 100 mM CaCl$_2$, 10 ml, 40° C., 24 hr | 600° C.(5° C./min), 1 hr | 100 mM ICl$_3$, 10 ml, 80° C., 24 hr |
| E7 | Ti—15Zr—4Nb—4Ta | | 100 mM CaCl$_2$, 10 ml, 40° C., 24 hr | 600° C.(5° C./min), 1 hr | 100 mM ICl$_3$, 10 ml, 80° C., 24 hr |
| C1 | Ti | [2] | 100 mM CaCl$_2$, 10 ml, 40° C., 24 hr | 600° C.(5° C./min), 1 hr | 1000 ppm Polyvinylpyrrolidone-iodine, 10 ml, 60° C., 24 hr |
| C2 | Ti | | 100 mM CaCl$_2$, 10 ml, 40° C., 24 hr | 600° C.(5° C./min), 1 hr | 100 mM NaI, 10 ml, 60° C., 24 hr |
| C3 | Ti | [2] | 100 mM ICl$_3$, 10 ml, 40° C., 24 hr | | |
| C4 | Ti | | 100 mM ICl$_3$, 10 ml, 40° C., 24 hr | 600° C.(5° C./min), 1 hr | |
| C5 | Ti | [2] | 1000 ppm Polyvinylpyrrolidone, 10 ml, 40° C., 24 hr | | |
| C6 | Ti | [2] | 50 mM HCl, 10 ml, 40° C., 24 hr | 600° C.(5° C./min), 1 hr | 1000 ppm Polyvinylpyrrolidone-iodine, 150 V, 3 min |

[1]E and C denote Example and Comparative Example, respectively.
[2]: The alkali treatment was performed by immersing the substrate in 5 ml of a 5M NaOHaq at 60° C. for 24 hr except E6 that was treated with same solution at 95° C.

[Composition Analysis]

A composition on a surface of the sample of each of Examples 1 to 7 and Comparative Examples 1 to 5 was analyzed by X-ray photoelectron spectroscopy at a measurement angle of 45°. As a result, as shown in Table 2, 1.4 to 7.5% by mass of calcium and 0.7 to 10.5% by mass of iodine were detected on the surfaces of the samples of the examples. It is presumed that a part of calcium was exchanged for iodine. On the other hand, no iodine was detected on the surfaces of the samples of Comparative Examples 1, 2, and 5. It is presumed that exchange of calcium for iodine was not caused. On the surface of the sample of Comparative Example 3, 10.2% by mass of iodine was detected. It is presumed that a part of sodium was exchanged for iodine. On the surface of the sample of Comparative Example 4, however, no iodine was detected. It is presumed that iodine was scattered by heating.

[Evaluation of Scratch Resistance]

Scratch resistance of the sample of each of Examples 1 to 7 and Comparative Examples 1 to 5 was measured with a scratch tester, and it was found, as shown in Table 2, that the scratch resistance of the sample not subjected to the heat treatment was as low as less than 10 mN but the scratch resistance of the sample subjected to the heat treatment at 600° C. was as high as 20 mN or more.

TABLE 2

| Sample | Element/mass % ||||||||| Scratch resistance/ mN | Apatite-forming ability |
|---|---|---|---|---|---|---|---|---|---|---|---|
| | O | Ti | Al | V | Zr | Nb | Ta | Ca | I | | |
| E1 | 42.7 | 46.1 | — | — | — | — | — | 2.6 | 8.6 | 33.3 | ◎ |
| E2 | 41.2 | 55.4 | — | — | — | — | — | 1.4 | 1.9 | 27.6 | ◎ |
| E3 | 39.0 | 52.4 | — | — | — | — | — | 6.2 | 2.3 | 25.3 | ◎ |
| E4 | 39.7 | 52.1 | — | — | — | — | — | 7.5 | 0.7 | 26.5 | ○ |
| E5 | 44.2 | 50.5 | — | — | — | — | — | 2.3 | 3.1 | 26.4 | ◎ |
| E6 | 40.0 | 46.3 | 0 | 0 | — | — | — | 3.2 | 10.5 | 41.5 | ◎ |
| E7 | 37.1 | 39.3 | — | — | 3.0 | 1.9 | 7.3 | 4.0 | 7.3 | 119.0 | ○ |
| C1 | 48.0 | 45.4 | — | — | — | — | — | 6.6 | 0.0 | — | — |
| C2 | 43.1 | 50.2 | — | — | — | — | — | 6.8 | 0.0 | — | — |
| C3 | 40.0 | 49.8 | — | — | — | — | — | 0 | 10.2 | 5.5 | — |
| C4 | 46.3 | 53.7 | — | — | — | — | — | 0 | 0 | 34.7 | — |
| C5 | 50.0 | 49.9 | — | — | — | — | — | 0 | 0 | 8.0 | — |

Figure 2:
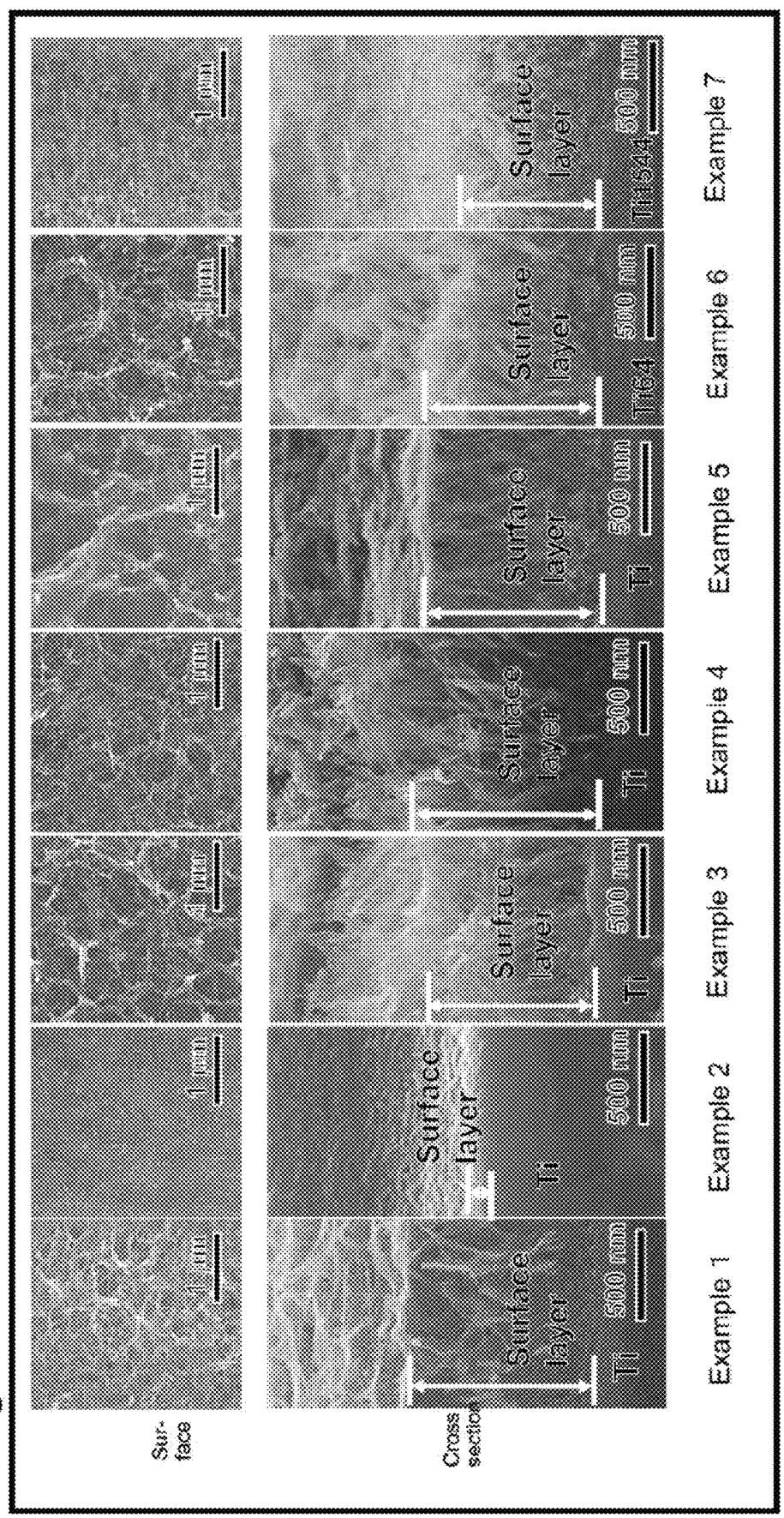
FIG. 2 illustrates electron micrographs of surfaces and cross-sections of samples of examples.

◎ Coverage of apatite on a sample surface after 3 days immersion in SBF: 90% or more
○ Coverage of apatite on a sample surface after 3 days immersion in SBF: 50% or more and less than 90%
Δ Coverage of apatite on a sample surface after 3 days immersion in SBF: 10% or more and less than 50%
X Coverage of apatite on a sample surface after 3 days immersion in SBF: less than 10%
— not performed The surface and cross-section of the sample of each example were observed with an electron microscope, resulting in finding, as illustrated in FIG. 2, that a film having a thickness of about 1 μm formed by entanglement of a large number of columnar crystalline masses extending in a direction crossing the principal plane of the substrate was formed on the surface of the sample of each of Examples 1, 3, 4, 5, 6, and 7. A surface film of the sample of Example 2 had a thickness of about 0.1 μm.

Figure 3:
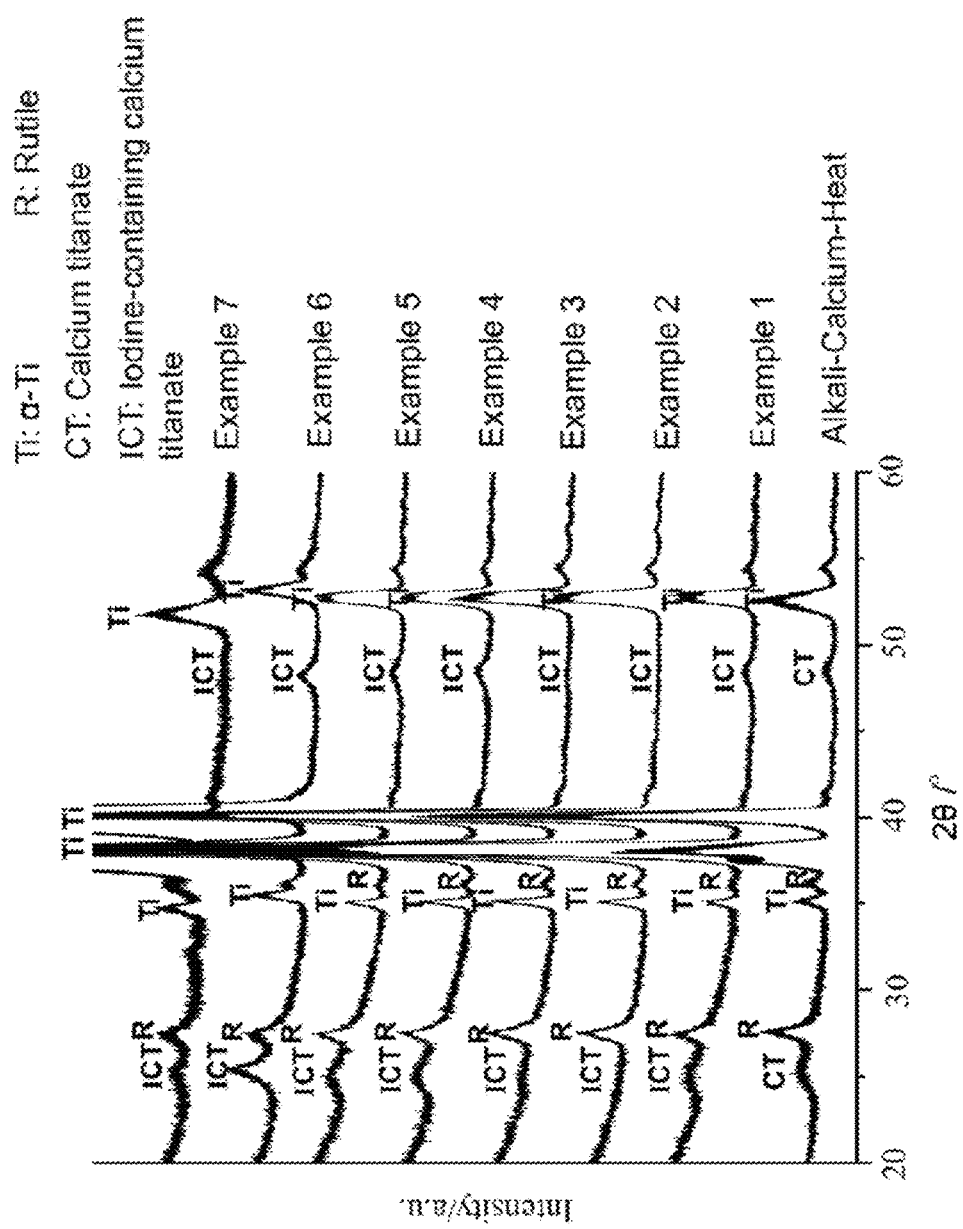
FIG. 3 is a chart illustrating thin film X-ray diffraction patterns of the samples of the examples.

Crystal structures of the surfaces of a control sample obtained under the same conditions as in Example 1 except that the iodine treatment was not performed and the samples of Examples 1 to 7 were checked by thin film X-ray diffraction. As a result, as illustrated in FIG. 3, peaks of calcium titanate and rutile-type titanium oxide were found in the control sample, and these peaks were also found in the samples of the examples. Accordingly, it was revealed that a part of calcium of calcium titanate was exchanged for iodine to form iodine-containing calcium titanate.

Figure 4:
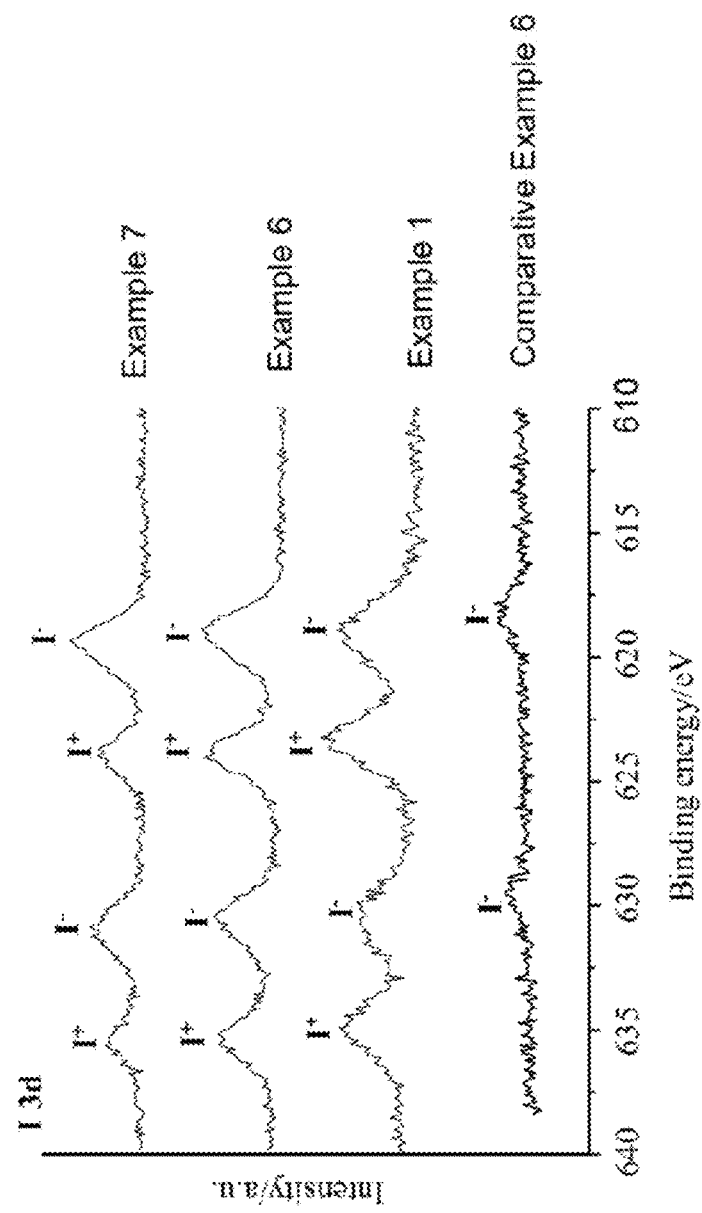
FIG. 4 is a chart illustrating results of X-ray photoelectron spectroscopy of iodine supported on the surfaces of the samples of Examples 1, 6, and 7 and Comparative Example 6.

The chemical state of iodine introduced onto the surface of the sample of each of Examples 1, 6, and 7 and Comparative Example 6 was checked by X-ray photoelectron spectroscopy (XPS). As illustrated in FIG. 4, peaks at 619 and 631 eV derived from a negative iodine ion as well as peaks at higher binding energy of 623 and 635 eV derived from a positive iodine ion were detected on the surface of the sample of each of Examples 1, 6, and 7. On the other hand, a peak derived from a negative iodine ion alone was detected on the surface of the sample of Comparative Example 6, and its intensity was lower than those of the examples, and hence its amount was presumed to be smaller.

[Evaluation of Apatite Forming Ability]

Figure 5:
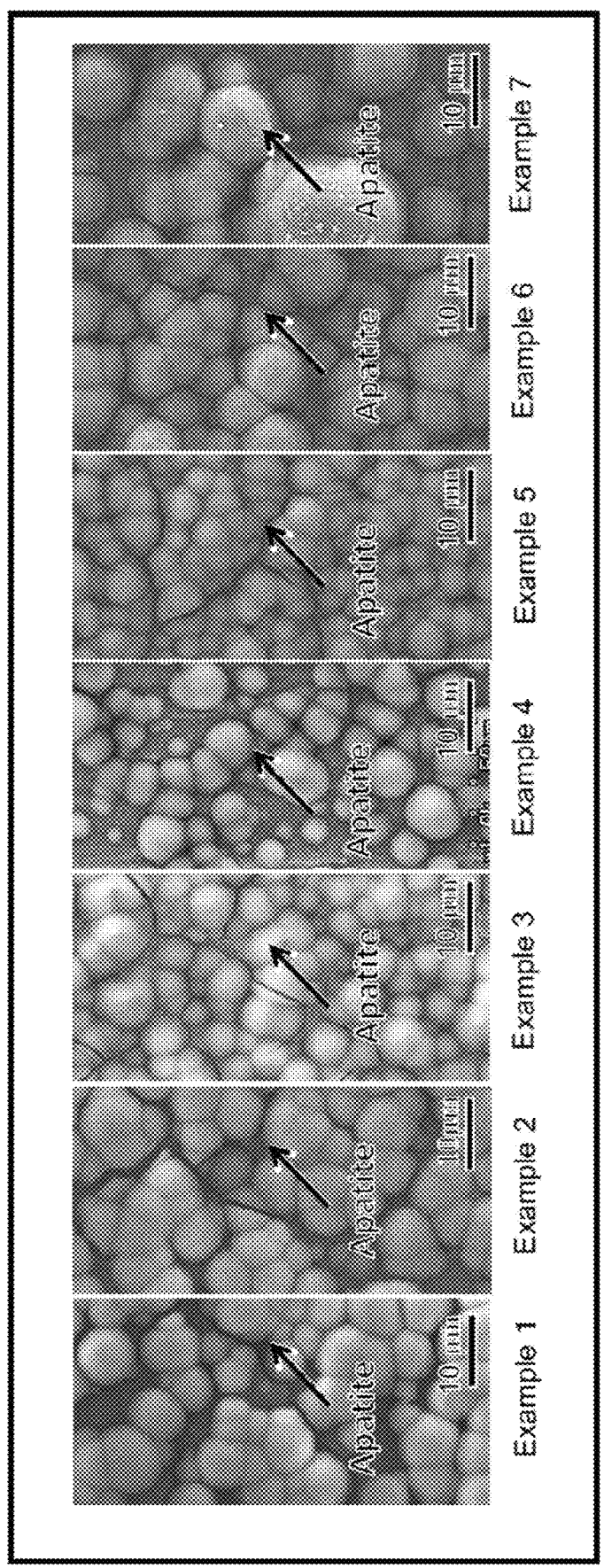
FIG. 5 illustrates electron micrographs of the surfaces of the samples of the examples obtained after 3 days immersion in a simulated body fluid.

The sample of each example was immersed in a simulated body fluid (SBF) according to ISO 23317 kept at 36.5° C. As a result, in the samples of all the examples, apatite was deposited to cover 50% or more of the surface within 3 days of the immersion in SBF as shown in Table 2 and FIG. 5. Accordingly, it was confirmed that these samples exhibit high apatite forming ability in a living body.

[Antibacterial Activity Evaluation 1]

The samples of Examples 1 and 3 and an untreated titanium plate were subjected to an antibacterial activity test against methicillin-resistant *Staphylococcus aureus* according to JIS Z2801:2012. The test was repeatedly performed twice, and an average number of colonies obtained in the test performed twice was calculated. Assuming that an initial average number of colonies was $4.2 \times 10^4/cm^2$, when the average number calculated 24 hours later was less than $10/cm^2$, the sample was evaluated as 4; when the average number was $10/cm^2$ or more and less than $100/cm^2$, the sample was evaluated as 3; when the average number was $100/cm^2$ or more and less than $1000/cm^2$, the sample was evaluated as 2; when the average number was $1000/cm^2$ or more and less than $10000/cm^2$, the sample was evaluated as 1; and when the average number was $10000/cm^2$ or more, the sample was evaluated as 0. A larger evaluation value means better antibacterial activity.

Figure 6:
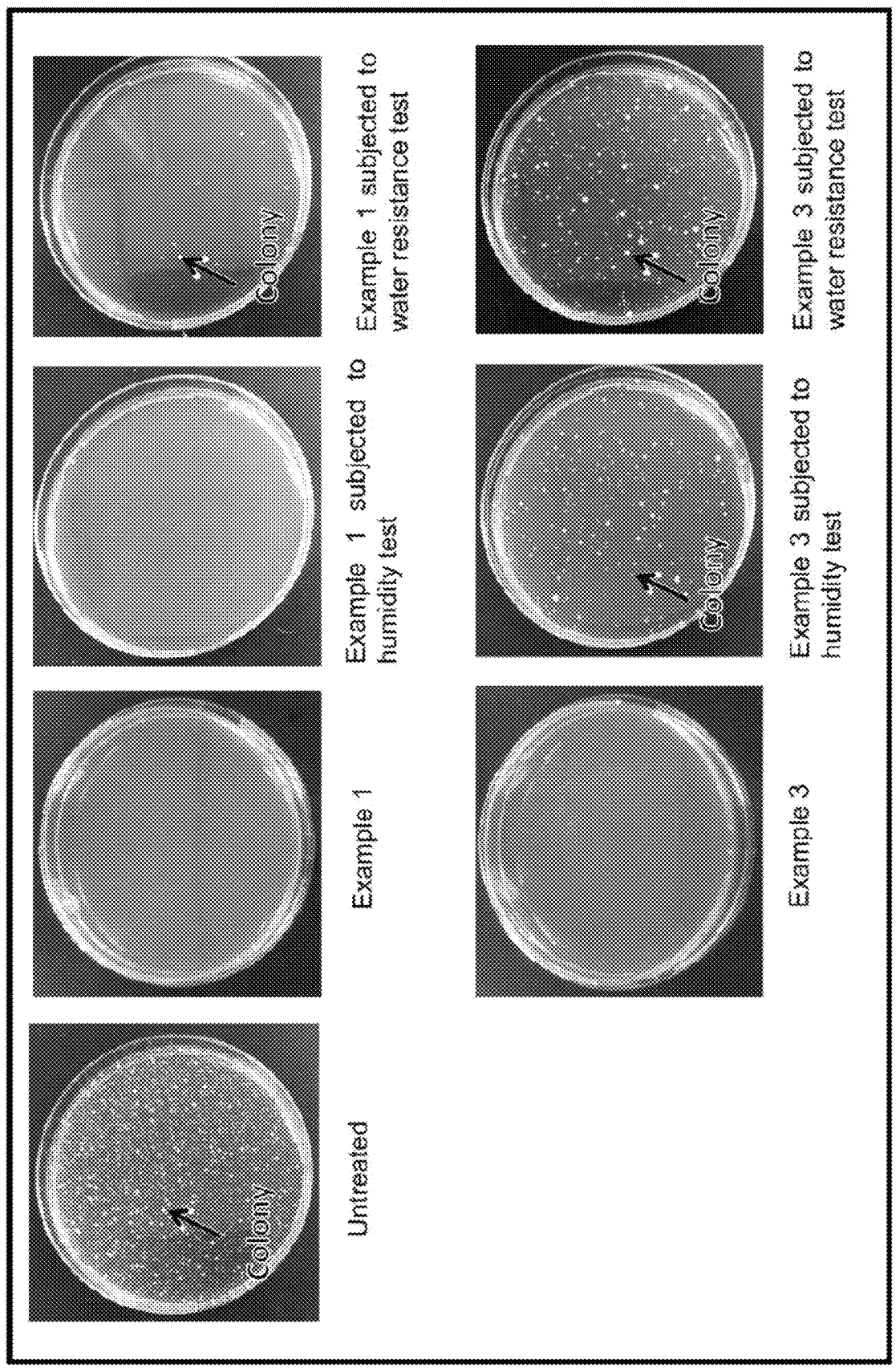
FIG. 6 illustrates evaluation results of antibacterial activity against methicillin-resistant *Staphylococcus aureus* of the samples of Examples 1 and 3.

As shown in Table 3 and FIG. 6, the untreated titanium plate was evaluated as 0, and thus did not exhibit antibacterial activity, but the samples of Examples 1 and 3 were both evaluated as 4, and thus exhibited high antibacterial activity. Besides, in order to check stability of the antibacterial effect, the samples of Examples 1 and 3 were subjected to a humidity test in which each sample was retained under a circumstance of 80° C. and relative humidity of 95% for 1 week, and to a water resistance test in which each sample was retained in phosphate buffered saline at 36.5° C. for 1 week while shaking at a rate of 50 strokes/min. The sample of Example 1 exhibited high antibacterial activity of an evaluation value of 3 or more even after any of the humidity and the water resistance tests, and thus was found to be excellent in stability in long-term storage and in a living body. The sample of Example 3 was found to still exhibit antibacterial activity although the evaluation value was reduced to 2 or 1 after the humidity and water resistance tests.

TABLE 3

| Sample | Average number of S. aureus/colony · $cm^{-2}$ | Antibacterial activity |
| --- | --- | --- |
| Untreated | $1.1 \times 10^4$ | 0 |
| Example 1 | 0 | 4 |
| Example 1 subjected to humidity test | 0 | 4 |

TABLE 3-continued

| Sample | Average number of S. aureus/colony · $cm^{-2}$ | Antibacterial activity |
| --- | --- | --- |
| Example 1 subjected to water resistance test | $5.5 \times 10$ | 3 |
| Example 3 | 0 | 4 |
| Example 3 subjected to humidity test | $5.5 \times 10^2$ | 2 |
| Example 3 subjected to water resistance test | $1.2 \times 10^3$ | 1 |

Antibacterial activity
4: Number of cultured colonies: less than $10/cm^2$
3: Number of cultured colonies: 10 to $99/cm^2$
2: Number of cultured colonies: 100 to $999/cm^2$
1: Number of cultured colonies: 1000 to $9999/cm^2$
0: Number of cultured colonies: $10000/cm^2$ or more

[Antibacterial Activity Evaluation 2]

The sample of Example 1 and an untreated titanium plate were subjected to an antibacterial activity test against *E. coli* according to JIS Z2801:2012 to be evaluated in the same manner as in Antibacterial Activity Evaluation 1. An initial average number of colonies was $4.1 \times 10^3/cm^2$.

As shown in Table 4, the untreated titanium plate was evaluated as 0, and thus did not exhibit antibacterial activity, but the sample of Example 1 was evaluated as 4, and thus exhibited high antibacterial activity. Besides, in order to check the stability of the antibacterial effect, the sample of Example 1 was subjected to the humidity test and the water resistance test. The sample of Example 1 exhibited antibacterial activity of an evaluation value of 2 or more even after any of the humidity and water resistance tests, and thus was found to be excellent in stability in long-term storage and in a living body.

TABLE 4

| Sample | Average number of E. coli/colony · $cm^{-2}$ | Antibacterial activity |
| --- | --- | --- |
| Untreated | $4.3 \times 10^4$ | 0 |
| Example 1 | 0 | 4 |
| Example 1 subjected to humidity test | 0 | 4 |
| Example 1 subjected to water resistance test | $2.3 \times 10^2$ | 2 |

Antibacterial activity
4: Number of cultured colonies: less than $10/cm^2$
3: Number of cultured colonies: 10 to $99/cm^2$
2: Number of cultured colonies: 100 to $999/cm^2$
1: Number of cultured colonies: 1000 to $9999/cm^2$
0: Number of cultured colonies: $10000/cm^2$ or more

[Cytotoxicity Test]

Figure 7:
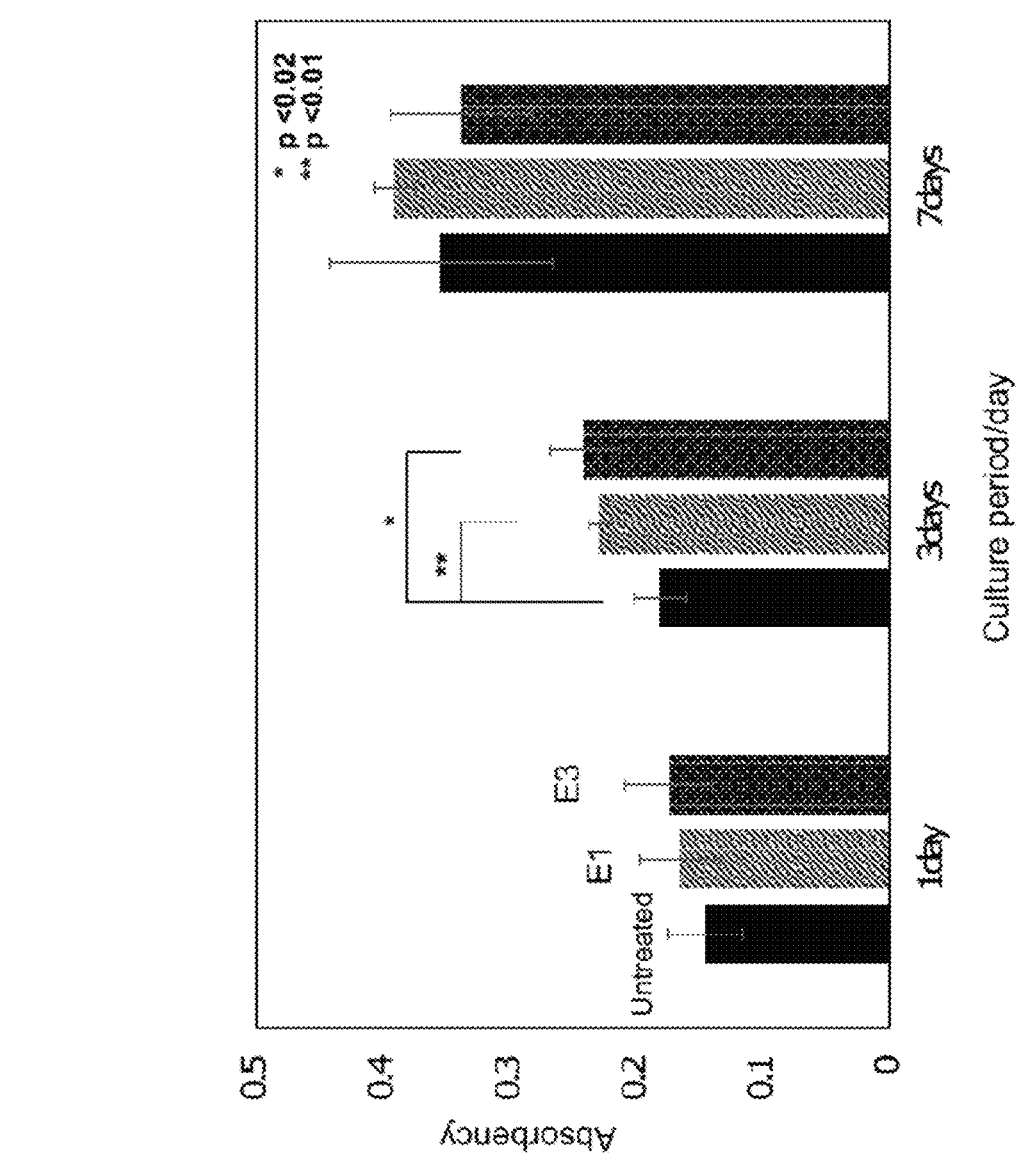
FIG. 7 is a graph illustrating the relationship between a culture period and absorbance obtained in a cell proliferation test of the samples of Examples 1 and 3 using MC3T3-E1 osteoblast.

In each of the samples of Examples 1 and 3 and an untreated titanium plate, MC3T3-E1 osteoblast was seeded at a seeding density of $8 \times 10^3$ cells/$cm^2$, and cultured for 1, 3, or 7 days. After that, a cell count reagent SF (manufactured by Nacalai Tesque, Inc., Kyoto, Japan) was added to the culture in a dropwise manner in a concentration of 100 µl/ml, and the resultant was retained in a 5% $CO_2$ incubator at 36.5° C. for 2 hours. Thereafter, an amount of formazan thus generated was quantitatively determined using an absorption photometer equipped with a filter of a wavelength of 450 nm. It is noted that four samples were used for each test condition to obtain an average of four measured values. A significant difference in cell proliferation ability of each sample group was evaluated by Student's t-test. As illustrated in FIG. 7, in the samples of the examples, as compared with the samples of the untreated titanium plate, there was no significant difference after 1 day culture, but significantly high proliferation ability was exhibited after 3 days culture. There was no significant difference after 7 days culture. It was revealed, based on these results, that the samples of Examples 1 and 3 do not exhibit cytotoxicity. Accordingly, it is presumed that these can be safely used in a living body. It is noted that significantly high proliferation ability was exhibited after 3 days culture but significant difference was not exhibited after 7 days culture probably because the culture reached confluence.

The invention claimed is:

1. A bone repair material, comprising:
   a substrate made of titanium or titanium alloy; and
   a titanate film on a surface of the substrate, the titanate film composed of a large number of crystalline masses having a crystal structure, and containing a calcium ion and an iodine ion,
   wherein at least a part of the iodine ions are positively charged.

2. The bone repair material according to claim 1, wherein the crystalline mass contains: a plurality of layers having a Ti—O skeleton; and the calcium ion and the iodine ion contained between the layers.

3. The bone repair material according to claim 1, wherein the titanate film has a thickness of 0.1 to 10 μm and a calcium ion concentration in a range of 0.1 to 10% by mass and an iodine ion concentration in a range of 0.1 to 15% by mass.

4. A method for producing the bone repair material according to claim 1, comprising the steps of:
   immersing a substrate made of titanium or titanium alloy in a first alkaline aqueous solution that does not contain a calcium ion or an iodine ion but contains one or more types of cations selected from a sodium ion and a potassium ion;
   immersing the substrate in a second aqueous solution containing a calcium ion;
   heating the substrate in the air; and
   immersing the substrate in a third aqueous solution containing an iodine ion.

5. The method according to claim 4, wherein the third aqueous solution is an aqueous solution of one or more compounds selected from the group consisting of iodine monochloride, iodine trichloride, hypoiodous acid, iodine monofluoride, iodine trifluoride, iodine pentafluoride, iodine heptafluoride, iodine monobromide, and iodine tribromide.

6. The method according to claim 4, wherein the third aqueous solution has a concentration of the iodine ion in a range of 1 to 5000 mM.

7. The method according to claim 4, wherein a temperature of the third aqueous solution is 20° C. or more, and a time for immersing the substrate in the third aqueous solution is 3 hours or more.

* * * * *